US008903728B2

(12) United States Patent
Maeda

(10) Patent No.: US 8,903,728 B2
(45) Date of Patent: Dec. 2, 2014

(54) SYSTEM FOR ENDOSCOPIC SURGERY HAVING A FUNCTION OF CONTROLLING THROUGH VOICE RECOGNITION

(71) Applicant: Olympus Medical Systems Corp., Tokyo (JP)

(72) Inventor: Yorito Maeda, Tokorozawa (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/866,697

(22) Filed: Apr. 19, 2013

(65) Prior Publication Data

US 2013/0281987 A1 Oct. 24, 2013

Related U.S. Application Data

(63) Continuation of application No. PCT/JP2012/076906, filed on Oct. 18, 2012.

(30) Foreign Application Priority Data

Oct. 25, 2011 (JP) ................................ 2011-233559

(51) Int. Cl.
| | | |
|---|---|---|
| A61B 17/00 | (2006.01) | |
| G10L 15/00 | (2013.01) | |
| A61B 1/00 | (2006.01) | |
| G10L 15/22 | (2006.01) | |
| G06F 3/16 | (2006.01) | |
| G10L 15/10 | (2006.01) | |
| G10L 21/034 | (2013.01) | |

(52) U.S. Cl.
CPC ......... *A61B 17/00234* (2013.01); *G10L 21/034* (2013.01); *A61B 1/00039* (2013.01); *G10L 15/22* (2013.01); *G06F 3/16* (2013.01); *G06F 3/167* (2013.01); *A61B 1/00* (2013.01); *G10L 15/10* (2013.01); *G10L 2015/227* (2013.01); *A61B 2017/00203* (2013.01); *G10L 2015/228* (2013.01); *G10L 15/00* (2013.01)
USPC .......................................................... 704/275

(58) Field of Classification Search
CPC .... A61B 17/00234; A61B 19/00; A61B 1/00; G06F 3/16; G06F 3/167; G10L 15/00; G10L 15/22
USPC .......................................................... 704/275
See application file for complete search history.

(56) References Cited

U.S. PATENT DOCUMENTS 5,893,064 A * 4/1999 Kudirka et al. ............ 704/270.1
6,463,361 B1 * 10/2002 Wang et al. .................... 700/258

(Continued)

FOREIGN PATENT DOCUMENTS

JP A-7-146696 6/1995
JP A-11-175095 7/1999

(Continued)

OTHER PUBLICATIONS

Aug. 7, 2014 Extended European Search Report issued in European Patent Application No. 12844263.9.

(Continued)

*Primary Examiner* — Michael N Opsasnick
(74) *Attorney, Agent, or Firm* — Oliff PLC

(57) ABSTRACT

In a system for endoscopic surgery, a storage unit stores a command for controlling a peripheral device and whether or not the command is valid or invalid in an associated manner for each operator and each procedure of an endoscopic surgery. A specification unit receives specification of an operator and a procedure. A conversion unit recognizes an input voice, and converts the voice into a voice command. A determination unit refers to the storage unit, and determines whether or not the voice command obtained by the conversion unit is identical to a command that has been set to be valid for the operator and the procedure specified by the specification unit. A transmission unit halts a transmission process to a peripheral device that corresponds to a command that has been determined to be invalid by the determination unit.

4 Claims, 17 Drawing Sheets

(56) References Cited

U.S. PATENT DOCUMENTS

| | | | |
|---|---|---|---|
| 6,535,854 B2* | 3/2003 | Buchner et al. | 704/275 |
| 6,587,824 B1* | 7/2003 | Everhart et al. | 704/275 |
| 7,249,025 B2* | 7/2007 | Junqua et al. | 704/271 |
| 8,014,756 B1* | 9/2011 | Henderson | 455/411 |
| 2002/0002465 A1* | 1/2002 | Maes | 704/275 |
| 2004/0236871 A1* | 11/2004 | Waxman | 710/1 |
| 2004/0260562 A1 | 12/2004 | Kujirai | |
| 2005/0154288 A1* | 7/2005 | Wang et al. | 600/407 |
| 2006/0058947 A1* | 3/2006 | Schalk | 701/207 |
| 2009/0177477 A1 | 7/2009 | Nenov et al. | |

FOREIGN PATENT DOCUMENTS

| | | |
|---|---|---|
| JP | A-2002-123291 | 4/2002 |
| JP | A-2002-132283 | 5/2002 |
| JP | A-2003-228394 | 8/2003 |
| JP | A-2004-199004 | 7/2004 |
| WO | WO 2006/057839 A1 | 6/2006 |

OTHER PUBLICATIONS

Aug. 28, 2014 Office Action issued in Chinese Patent Application No. 201280014971.0 (with partial English translation).

* cited by examiner

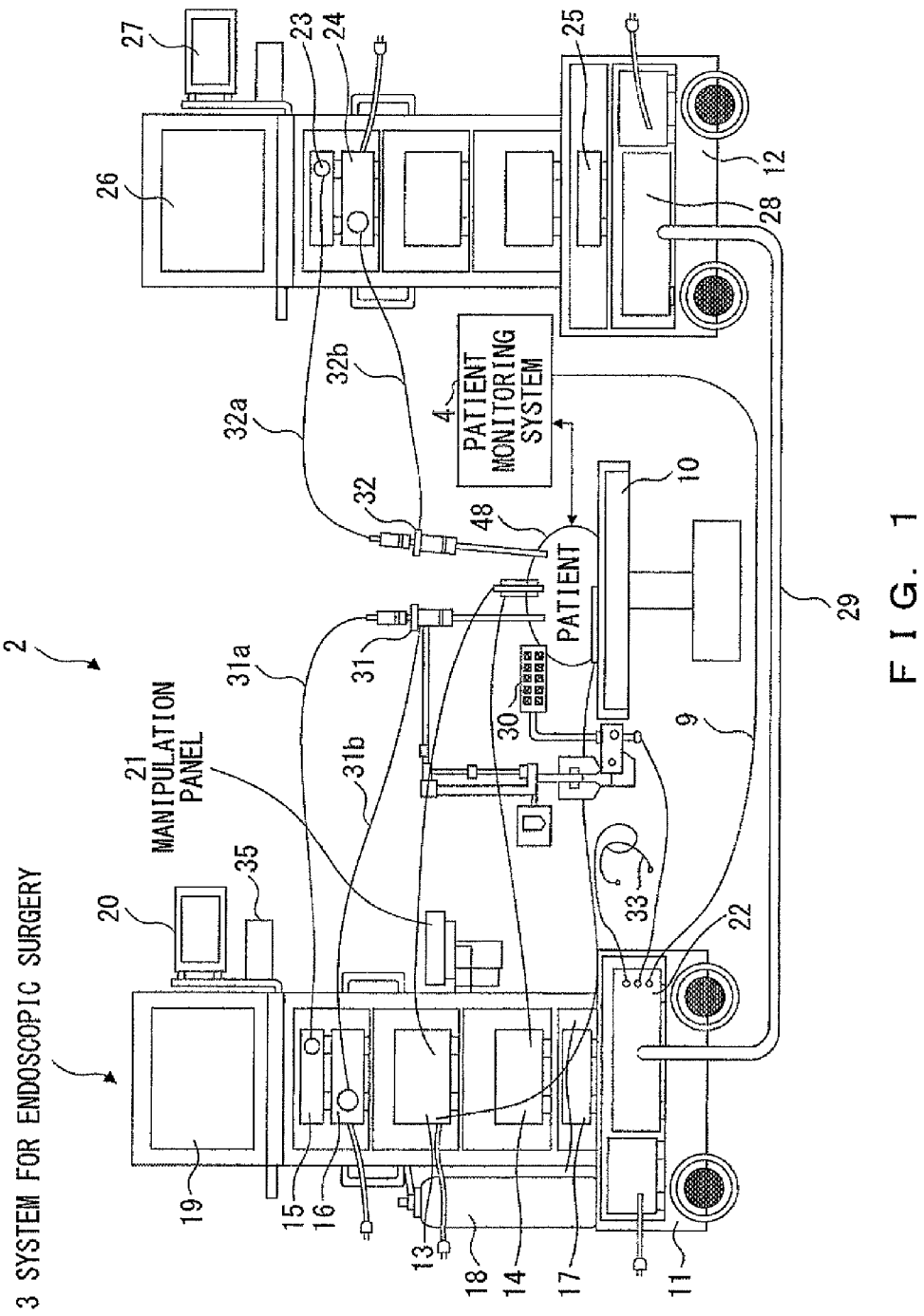
F I G. 1

FIG. 4

| OPERATOR INFORMATION | Dr. A | |
|---|---|---|
| PROCEDURE INFORMATION | LAPAROSCOPIC CHOLECYSTECTOMY | |
| VOICE RECOGNITION COMMAND | | VALID/INVALID |
| FREEZE | | INVALID |
| RELEASE | | VALID |
| PNEUMOPERITONEUM APPARATUS | | VALID |
| PRESSURE | | VALID |
| INCREASE POWER FOR ELECTROCAUTERY SCALPEL | | INVALID |
| DECREASE POWER FOR ELECTROCAUTERY SCALPEL | | INVALID |
| WHITE BALANCE | | VALID |
| TURN ON LIGHT SOURCE | | VALID |
| START RECORDING | | INVALID |
| . . . | | . |
| . . . | | . |
| . . . | | . |

| OPERATOR INFORMATION | Dr. A | |
|---|---|---|
| PROCEDURE INFORMATION | LAPAROSCOPIC CHOLECYSTECTOMY | |
| VOICE RECOGNITION COMMAND | VALID/INVALID | |
| FREEZE | INVALID | |
| RELEASE | VALID | |
| PNEUMOPERITONEUM APPARATUS | VALID | |
| PRESSURE | VALID | |
| INCREASE POWER FOR ELECTROCAUTERY SCALPEL | INVALID | |
| DECREASE POWER FOR ELECTROCAUTERY SCALPEL | INVALID | |
| WHITE BALANCE | VALID | |
| TURN ON LIGHT SOURCE | VALID | |
| START RECORDING | INVALID | |
| . | . | |
| . | . | |
| . | . | |

F I G. 5

| | | |
|---|---|---|
| OPERATOR INFORMATION | Dr. A | |
| PROCEDURE INFORMATION | LADG | |
| VOICE RECOGNITION COMMAND | VALID/INVALID | |
| FREEZE | INVALID | |
| RELEASE | INVALID | |
| PNEUMOPERITONEUM APPARATUS | VALID | |
| PRESSURE | VALID | |
| INCREASE POWER FOR ELECTROCAUTERY SCALPEL | VALID | |
| DECREASE POWER FOR ELECTROCAUTERY SCALPEL | VALID | |
| WHITE BALANCE | VALID | |
| TURN ON LIGHT SOURCE | VALID | |
| START RECORDING | INVALID | |
| . | . | |
| . | . | |
| . | . | |

F I G. 5 (Continued)

| OPERATOR INFORMATION | Dr. B |
|---|---|
| PROCEDURE INFORMATION | LAC |

| VOICE RECOGNITION COMMAND | VALID/INVALID |
|---|---|
| FREEZE | VALID |
| RELEASE | VALID |
| PNEUMOPERITONEUM APPARATUS | VALID |
| PRESSURE | VALID |
| INCREASE POWER FOR ELECTROCAUTERY SCALPEL | INVALID |
| DECREASE POWER FOR ELECTROCAUTERY SCALPEL | INVALID |
| WHITE BALANCE | VALID |
| TURN ON LIGHT SOURCE | VALID |
| START RECORDING | VALID |
| . | . |
| . | . |
| . | . |

F I G. 5 (Continued)

| | | VALID/INVALID |
|---|---|---|
| OPERATOR INFORMATION (52) | Dr. A | |
| PROCEDURE INFORMATION (53) | LAPAROSCOPIC CHOLECYSTECTOMY | |
| SCENE INFORMATION (54) | LAPAROTOMY | |
| VOICE RECOGNITION COMMAND (55) | | VALID/INVALID (56) |
| FREEZE | | INVALID |
| RELEASE | | VALID |
| PNEUMOPERITONEUM APPARATUS PRESSURE | | VALID |
| | | VALID |
| INCREASE POWER FOR ELECTROCAUTERY SCALPEL | | VALID |
| DECREASE POWER FOR ELECTROCAUTERY SCALPEL | | VALID |
| WHITE BALANCE | | INVALID |
| TURN ON LIGHT SOURCE | | INVALID |
| START RECORDING | | VALID |
| ... | | ... |

| | | VALID/INVALID |
|---|---|---|
| PROCEDURE INFORMATION (52) | Dr. A | |
| OPERATOR INFORMATION (53) | LAPAROSCOPIC CHOLECYSTECTOMY | |
| SCENE INFORMATION (54) | SUTURA | |
| VOICE RECOGNITION COMMAND (55) | | VALID/INVALID (56) |
| FREEZE | | INVALID |
| RELEASE | | VALID |
| PNEUMOPERITONEUM APPARATUS PRESSURE | | VALID |
| | | VALID |
| INCREASE POWER FOR ELECTROCAUTERY SCALPEL | | INVALID |
| DECREASE POWER FOR ELECTROCAUTERY SCALPEL | | INVALID |
| WHITE BALANCE | | VALID |
| TURN ON LIGHT SOURCE | | VALID |
| START RECORDING | | INVALID |
| ... | | ... |

FIG. 6

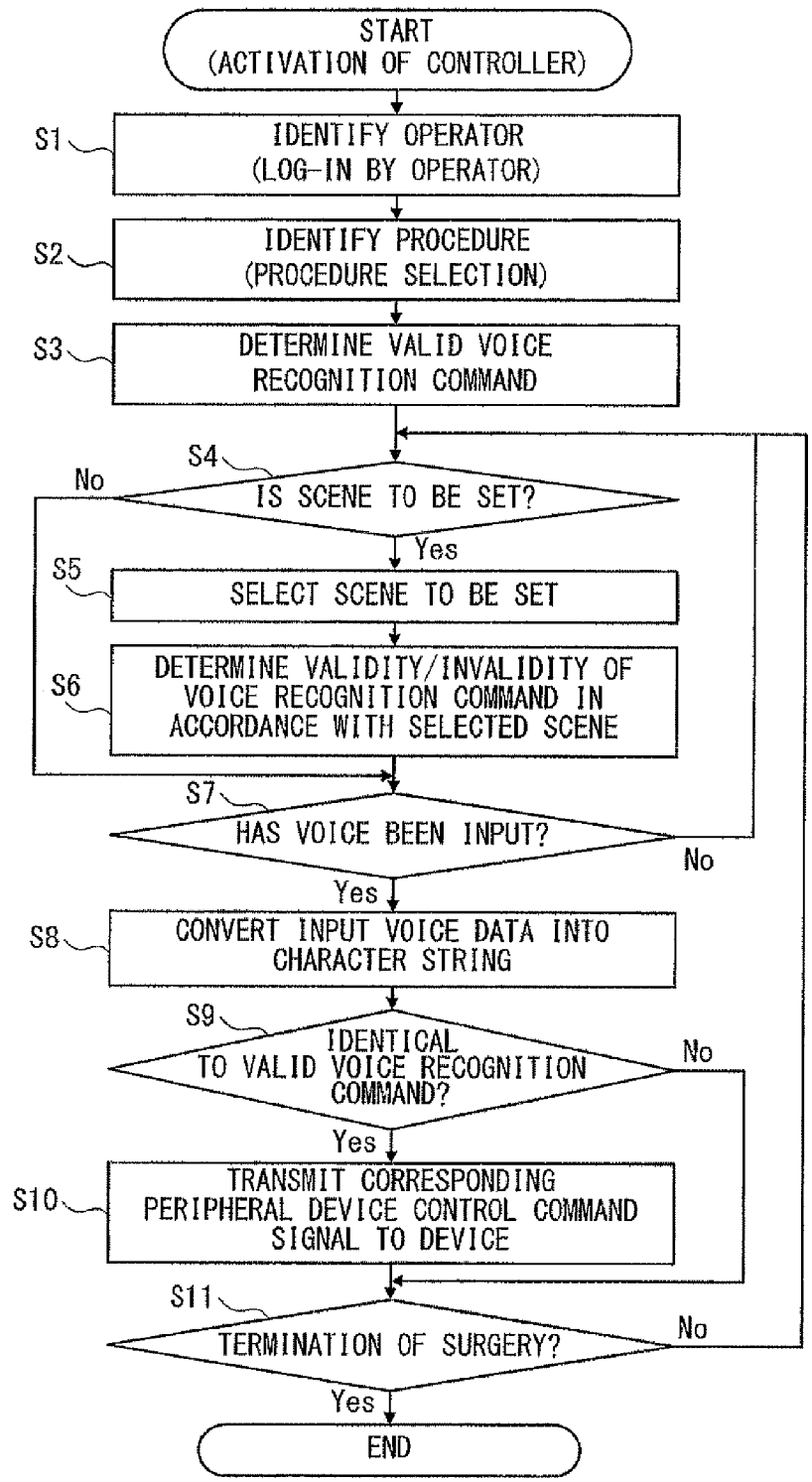
F I G. 7

| INPUT VOICE 64 68 | FIRST CHARACTER 65 69 | LAST CHARACTER 66 70 | CHARACTER NUMBER 67 71 | CHARACTER NUMBER THRESHOLD (CHARACTER NUMBER/2) 72 |
|---|---|---|---|---|
| でんぴめすーりょあぶ | で | ぶ | 10 | |
| VOICE RECOGNITION COMMAND | FIRST CHARACTER | LAST CHARACTER | CHARACTER NUMBER | |
| フリーズ | ふ | ず | 4 | 2 |
| レリーズ | れ | ず | 4 | 2 |
| 気腹器送気 | き | き | 7 | 3 |
| 圧力 | あ | く | 4 | 2 |
| 電気メス出力アップ | で | ぷ | 12 | 6 |
| 電気メス出力ダウン | で | ん | 12 | 6 |
| ホワイトバランス | ほ | す | 8 | 4 |
| 光源オン | こ | ん | 6 | 3 |
| 録画開始 | ろ | し | 6 | 3 |
| . | . | . | . | . |
| . | . | . | . | . |
| . | . | . | . | . |

FIG. 10 (Continued)

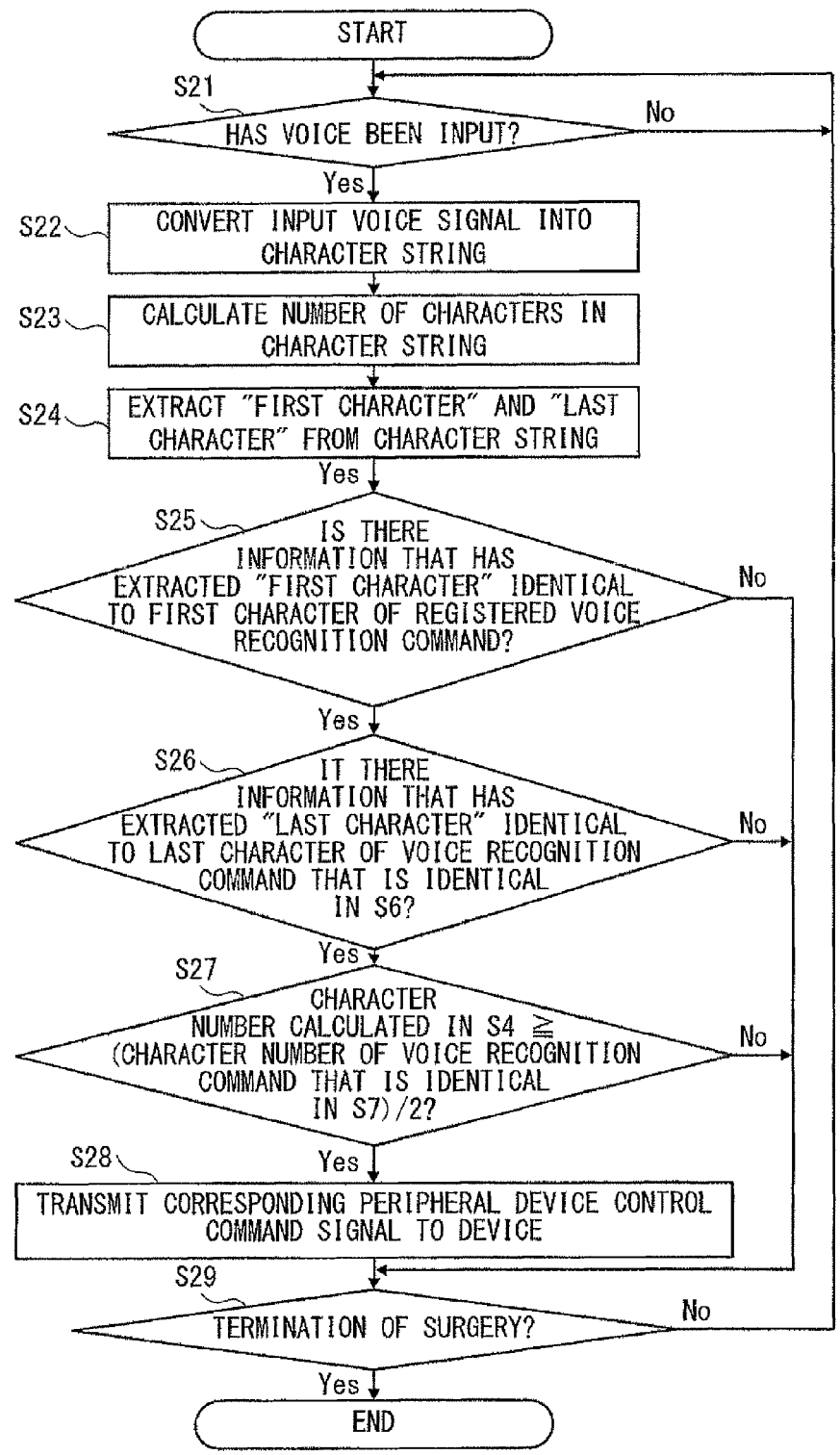
F I G. 1 1

SYSTEM FOR ENDOSCOPIC SURGERY HAVING A FUNCTION OF CONTROLLING THROUGH VOICE RECOGNITION

CROSS-REFERENCE TO RELATED APPLICATIONS

This application is based upon and claims the benefit of priority of the prior Japanese Patent Application No. 2011-233559, filed Oct. 25, 2011, the entire contents of which are incorporated herein by reference.

This is a Continuation Application of PCT Application No. PCT/JP2012/076906, filed Oct. 18, 2012, which was not published under PCT Article 21(2) in English.

FIELD

The present invention is related to a system for endoscopic surgery that has a function of controlling, through voice recognition, a connected peripheral device.

BACKGROUND

Usually, in an endoscopic surgery, which uses an endoscopic device, the operator performs treatment while having in both hands treatment tools that are inserted into the body cavity. When the operator desires to change parameters or the like of peripheral devices during the surgery, he or she requests an assistant or the like to manipulate a operation panel or the like disposed in a non-sterilization area, or in some cases, he or she can manipulate switches or the like disposed near to himself or herself (sterilization area). However, there are cases in which the operator desires to perform fine adjustment by himself or herself without requesting that other people perform manipulation or cases in which manipulation is difficult to perform due to positions or orientations of treatment tools.

As means for solving the above problem, there is a technique, according to Japanese Laid-open Patent Publication No. 2002-123291, regarding a system for endoscopic surgery having a voice recognition function and performing the changing of parameters, etc., of a peripheral device in accordance with a command input via the voice of the operator.

A technique disclosed by, for example, Japanese Laid-open Patent Publication No. 2002-123291, performs voice recognition based on pattern recognition. Specifically, voice commands are registered beforehand in the system and a command vocalized by an operator is compared with the registered voice commands. When the voice command input by the operator and a registered command are identical to each other, that voice command is recognized.

As for a voice recognition technique, Japanese Laid-open Patent Publication No. 2004-199004, for example, has disclosed a technique by which a difference is calculated between the level data of an input voice (vocal volume) and the level data that was obtained immediately previously so as to perform processes in accordance with the result of comparison between the difference and a reference value. Also, Japanese Laid-open Patent Publication No. 07-146696 has disclosed a technique of measuring recognition ratios. Japanese Laid-open Patent Publication No. 2003-228394 has disclosed, as a technique of performing a voice recognition process on the content input via voice, a technique of determining a noun input by a user via voice on the basis of the first character and the number of characters.

SUMMARY

A system for endoscopic surgery according to one aspect of the present invention is a system for endoscopic surgery having a function of controlling, through voice recognition, a connected peripheral device, including a storage unit that stores a command for controlling the peripheral device and whether or not the command is valid or invalid in an associated manner for each operator and each procedure of an endoscopic surgery; a specification unit that receives specification of the operator and the procedure; a conversion unit that recognizes an input voice, and converts the voice into a voice command; a determination unit that refers to the storage unit, and determines whether or not the voice command obtained by the conversion unit is identical to a command that has been set to be valid for the operator and the procedure specified by the specification unit; and a transmission unit that halts a transmission process to a peripheral device that corresponds to a command that has been determined to be invalid by the determination unit.

A system for endoscopic surgery according to one aspect of the present invention is a system for endoscopic surgery having a function of controlling, through voice recognition, a connected peripheral device, including a storage unit that stores a command for controlling the peripheral device and whether or not the command is valid or invalid in an associated manner for each operator and each procedure of an endoscopic surgery; a specification unit that receives specification of the operator and the procedure; a conversion unit that recognizes an input voice, and converts the voice into a voice command; a determination unit that refers to the storage unit, and determines whether or not the voice command obtained by the conversion unit is identical to a command that has been set to be valid for the operator and the procedure specified by the specification unit; and a transmission unit that transmits a command that has been determined to be identical by the determination unit, to a corresponding peripheral device.

A system for endoscopic surgery according to one aspect of the present invention is a system for endoscopic surgery having a function of controlling, through voice recognition, a connected peripheral device, including a storage unit that stores a command for controlling the peripheral device and whether or not the command is valid or invalid in an associated manner for each room in which an endoscopic surgery is performed; a specification unit that receives information for identifying a room in which an endoscopic surgery is performed; a conversion unit that recognizes an input voice, and converts the voice into a voice command; a determination unit that refers to the storage unit, and determines whether or not the voice command obtained by the conversion unit is identical to a command that has been set to be valid for the room specified by the specification unit; and a transmission unit that transmits a command determined to be identical by the determination unit, to a corresponding peripheral device.

BRIEF DESCRIPTION OF DRAWINGS

The present invention will be more apparent from the following detailed description when the accompanying drawings are referenced.

FIG. 1 shows an overall configuration of a system for endoscopic surgery according to a first embodiment;

FIG. 4 shows a method of registering the validity or invalidity of voice recognition commands;

FIG. 5 exemplifies voice manipulation setting information set for each piece of operator information and procedure information;

FIG. 6 exemplifies voice manipulation setting information set for each piece of operator information, procedure information, and scene;

FIG. 7 is a flowchart showing a process in which the control unit of the system controller according to the first embodiment controls peripheral devices on the basis of voice recognition;

FIG. 11 shows a flowchart explaining a process in which a control unit of a system controller according to the second embodiment controls peripheral devices on the basis of voice recognition;

DESCRIPTION OF EMBODIMENTS

Figure 2:
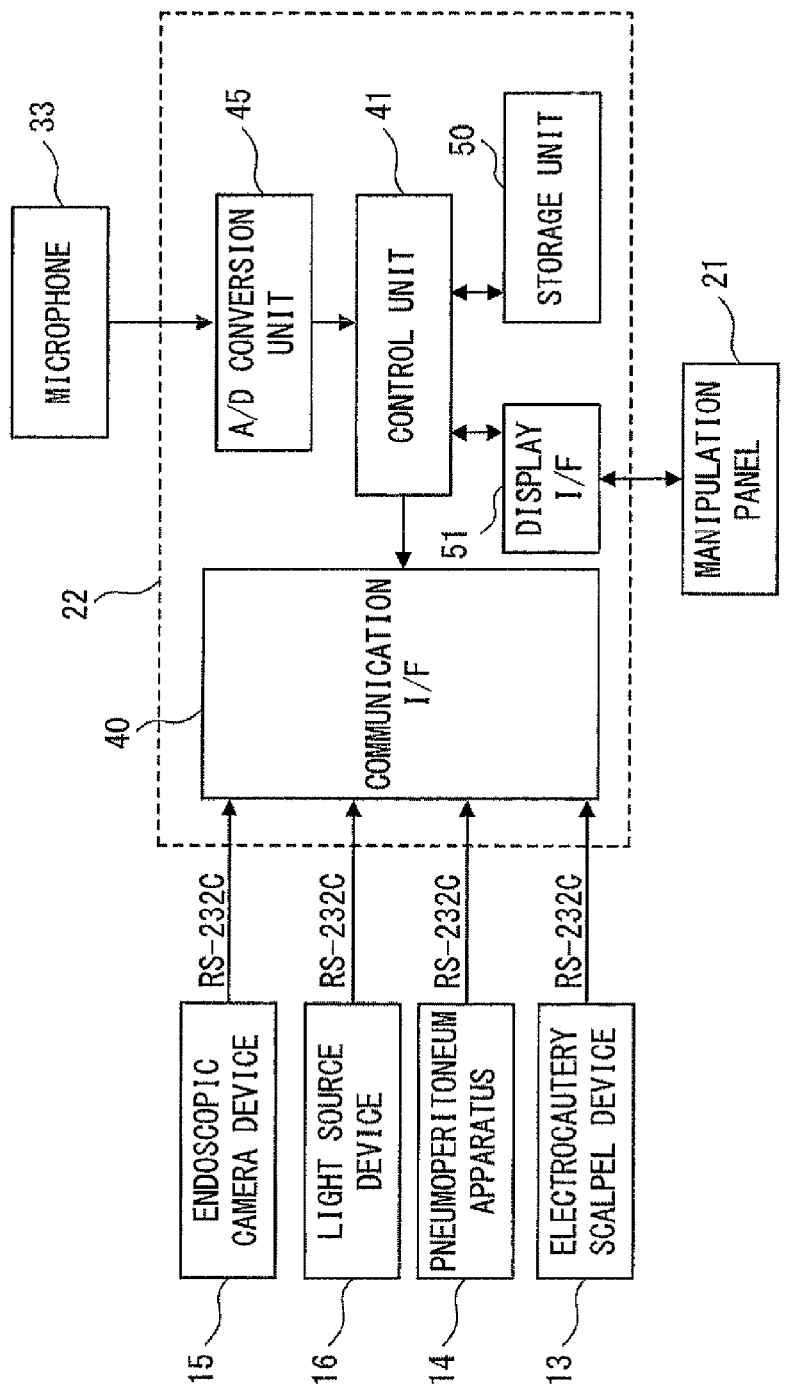
FIG. 2 is a block diagram of a system controller according to the first embodiment.

Hereinafter, detailed explanations will be given for the embodiments of the present invention by referring to the drawings.

<First Embodiment>

FIG. 1 shows an overall configuration of a system for endoscopic surgery according to the present embodiment. A system for endoscopic surgery 3 shown in FIG. 1 is installed in a surgery room 2 together with a patient bed 10, on which a patient 48 is to be laid. The system for endoscopic surgery 3 includes a first cart 11 and a second cart 12, each of which mounts devices and the like used for endoscopic surgeries.

The first cart 11 mounts devices such as an electrocautery scalpel device 13, a pneumoperitoneum apparatus 14, an endoscopic camera device 15, a light source device 16 and video tape recorder (VTR hereinafter) 17 or the like type of device, and a gas tank 18.

The endoscopic camera device 15 is connected to a first endoscope 31 through a camera cable 31a.

The light source device 16 is connected to the first endoscope through a light guide cable 31b.

The VTR 17 performs recordings or the like of endoscopic images obtained by the first endoscope 31 or the like.

The gas tank 18 has been charged with a gas such as carbon dioxide to be used in endoscopic surgeries.

The electrocautery scalpel device 13 and the pneumoperitoneum apparatus 14 are medical instruments used for endoscopic surgeries, and these instruments can be controlled by changing parameters and the like in accordance with manipulation commands from a connected system controller 22.

Also, the first cart 11 mounts a display device 19, a (first) concentrated display panel 20, a manipulation panel 21, and the like.

The display device 19 is a device for displaying endoscopic images or the like, and is, for example, a TV monitor. The concentrated display panel 20 is a display unit that can selectively display all pieces of data treated by the system for endoscopic surgery 3. The manipulation panel 21 is a concentrated manipulation device which includes a display unit such as, for example, a liquid crystal display device or the like and a touch sensor or the like provided on the display unit in an integrated manner, and through which nurses and the like in the non-sterilization area (unclean area) manipulate peripheral devices or the like of the system for endoscopic surgery 3.

Further, the first cart 11 mounts the system controller 22. As described above, the system controller 22 controls various peripheral devices connected to the system for endoscopic surgery 3. In the configuration example shown in FIG. 1, the system controller 22 is connected to the electrocautery scalpel device 13, the pneumoperitoneum apparatus 14, the endoscopic camera device 15, the light source device 16, and the VTR 17 through a communication line (not shown). A headset-type microphone 33 can be connected to the system controller 22. The system controller 22 recognizes an input, made into the microphone 33, of a command via the voice of an operator, and transmits manipulation commands to connected various peripheral devices in accordance with the recognized command so as to control the peripheral devices.

Also, an RFID (Radio Frequency Identification) terminal 35 is provided in the first cart 11, and reads and writes individual identification information wirelessly from/to ID (Identification) tags embedded in treatment tools or the like such as the first endoscope 31, the electrocautery scalpel device 13, and the like.

The second cart 12 mounts an endoscopic camera device 23, a light source device 24, an image processing device 25, a display device 26, and a (second) concentrated display panel 27.

The endoscopic camera device 23 is connected to a second endoscope 32 through a camera cable 32a.

The light source device 24 is connected to the second endoscope 32 through a light guide cable 32b.

The display device 26 is a device for displaying endoscopic images obtained by the endoscopic camera device 23, and is, for example, a TV monitor. The concentrated display panel 27 is a display unit that can selectively display all pieces of data treated by the system for endoscopic surgery 3.

The endoscopic camera device 23, the light source device 24, and the image processing device 25 are connected through a communication line (not shown) to a relay unit 28 mounted on the second cart 12. The relay unit 28 is connected to the above described system controller 22 through a relay cable 29.

As described above, the system controller 22 performs concentrated control of the electrocautery scalpel device 13, the pneumoperitoneum apparatus 14, the endoscopic camera device 15, the light source device 16, and the VTR 17 mounted on the first cart 11, and the endoscopic camera device 23, the light source device 24, and the image processing device 25 mounted on the second cart 12. Accordingly, the system controller 22 is configured to be able to display a setting window for information such as setting conditions of connected devices, manipulation switches, and the like on the liquid crystal display of the manipulation panel 21 when communication is being made between the system controller 22 and these devices. The system controller 22 allows manipulation input such as changing or the like of setting values when a desired manipulation switch is touched to manipulate a touch sensor in a prescribed area.

A remote controller 30 is a second concentrated manipulation device to be manipulated by an operating surgeon, who is the operator in the sterilization area. The remote controller 30 controls, via the system controller 22, manipulations of other devices that are communicating with the system controller 22.

The system controller 22 is connected to a patient monitoring system 4 through a cable 9. The system controller 22 can analyze biological information held by the patient monitoring system 4 so as to make a desired display device display an analysis result.

Also, the system controller 22 is provided with a communication unit such as an infrared communication port or the like (not shown) in FIG. 1. A communication unit such as an infrared port or the like is disposed in, for example, a spot near the display device 19 or the like that can be irradiated with infrared rays easily. The communication unit or the like is connected to the system controller 22 through a cable.

When system controller 22 of the system for endoscopic surgery 3 shown in FIG. 1 has determined that a voice command for controlling a prescribed peripheral device has been input on the basis of a voice input by an operator through the microphone 33, the system controller 22 transmits a corresponding manipulation command to the peripheral device. When it is determined whether or not a voice command has been input, voice recognition is performed only for voice commands that have been registered beforehand as being "valid" as voice commands, and corresponding commands are transmitted to the peripheral devices.

Hereinafter, a method of performing voice recognition of a voice input through the system controller 22 of the system for endoscopic surgery 3 according to the present embodiment so as to perform control will be explained specifically.

In the explanations below, input voices that are recognized as voice commands for manipulating peripheral devices are referred to as "voice recognition commands", and commands transmitted through a communication line to peripheral devices are referred to as "manipulation commands".

FIG. 2 is a block diagram of the system controller 22 according to the present embodiment. The system controller 22 shown in FIG. 2 includes a communication interface ("communication I/F", hereinafter) 40, an A/D conversion unit 45, a display interface ("display I/F", hereinafter) 51, a storage unit 50, and a control unit 41.

The A/D conversion unit 45 converts, into digital signals, analog voice signals input through the microphone 33 connected to the system controller.

The display I/F 51 is an interface that makes the manipulation panel 21 display the GUI (Graphical User Interface) and transmits to the control unit 41 signals of touch manipulations by a user input through the manipulation panel 21. The display I/F 51 receives specifications of, for example, an operator who uses the system for endoscopic surgery 3, procedures or the like used by the operator, and other information.

The communication I/F 40 is a communication interface with peripheral devices such as the endoscopic camera device 15, the light source device 16, the pneumoperitoneum apparatus 14, the electrocautery scalpel device 13, and the like. FIG. 2 only shows devices directly connected to the system controller 22 in FIG. 1, omitting devices connected through the relay cable 29 or the relay unit 28.

The control unit 41 obtains, via the communication I/F 40, parameters of connected devices (peripheral devices) such as the endoscopic camera device 15 or the like, and makes the manipulation panel 21 display the obtained parameters via the display I/F 51. Also, the control unit 41 transmits manipulation commands via the communication I/F 40 in accordance with signals of touch manipulations on the manipulation panel 21 received by the display I/F 51 or voice signals input through the A/D conversion unit 45, and controls peripheral devices. When the control unit 41 has recognized that a voice recognition command has been input through the microphone 33, the control unit 41 makes the manipulation panel 21 display corresponding manipulation commands through the display I/F 51. Thereafter, the control unit 41 controls peripheral devices via the communication I/F 40 in accordance with the manipulation commands.

The storage unit 50 stores information necessary for the control unit 41 to perform control or the like of peripheral devices. Specifically, the storage unit 50 stores voice recognition commands for comparison with character strings obtained from voice signals input through the A/D conversion unit 45, information for identifying operators and procedures, and information representing whether each voice recognition command is set to be valid or invalid, which is associated with voice recognition commands or the like. Detailed explanations will be given for this information that can be stored in the storage unit 50 by referring to FIG. 5, FIG. 6, and others.

Figure 3:
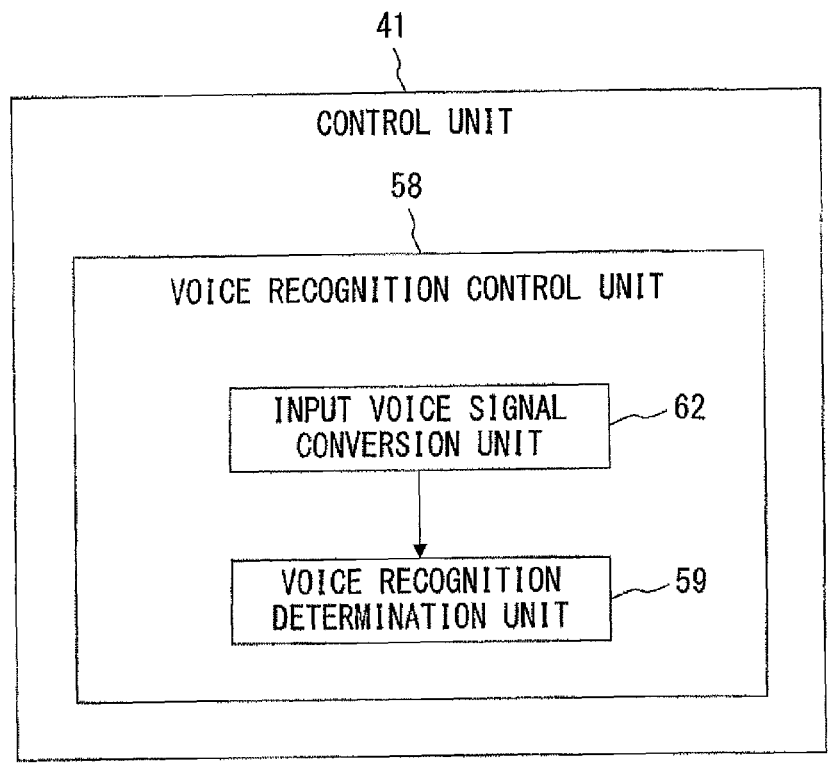
FIG. 3 is a function block diagram of a control unit according to the first embodiment.

FIG. 3 is a function block diagram of the control unit 41 according to the present embodiment. As shown in FIG. 3, according to the present embodiment, the control unit 41 includes a voice recognition control unit 58, and the voice recognition control unit 58 includes an input voice signal conversion unit 62 and a voice recognition determination unit 59.

The voice recognition control unit 58 converts voice signals input through the A/D conversion unit 45 shown in FIG. 2 into a character string in the input voice signal conversion unit 62. The voice recognition determination unit 59 determines whether or not the character string obtained by the conversion process performed by the input voice signal conversion unit 62 is identical to a voice recognition command that has been set to be valid in accordance with information stored in the storage unit 50 in FIG. 2. Hereinafter, determination by the voice recognition determination unit 59 may also be referred to as voice recognition determination.

In the system for endoscopic surgery 3 according to the present embodiment, whether or not voice recognition commands that can control peripheral devices are valid or invalid is stored in the storage unit 50 beforehand for each operator and procedure. When the voice recognition control unit 58 compares a character string obtained from input voice signals with information stored in the storage unit 50 and has determined to be identical to a voice recognition command that has been set to be valid, the control unit 41 transmits the corresponding manipulation command to peripheral devices. When the character string has been determined to be not identical to a voice recognition command set to be valid or when the character string has been determined to be identical to a voice recognition command but a manipulation command is set to be invalid as the voice recognition command, the control unit 41 stops the process of transmitting the corresponding command to peripheral devices.

FIG. 4 shows a method of registering the validity or invalidity of voice recognition commands. FIG. 4 shows an example of a window for prompting a user to set the validity/invalidity of each voice recognition command used for a prescribed procedure by a prescribed operator in the display unit of the manipulation panel 21, by the GUI prepared by the system controller 22 beforehand.

FIG. 4 shows a state in which the setting window is open for voice commands corresponding to operator information 52 and procedure information 53 specified by an operator or the like via the manipulation panel 21. The operator information 52 is information for identifying an operator who performs an endoscopic surgery, and the procedure information 53 is information for identifying a procedure used for the endoscopic surgery. For each manipulation command that can be transmitted from the system controller 22 to peripheral devices when "laparoscopic cholecystectomy" surgery represented by the procedure information 53 is to be performed by an operator "Dr. A" represented by the operator information 52, the validity or invalidity of voice recognition is set in the window or the like of the manipulation panel 21 shown in FIG. 4.

In accordance with this, voice recognition commands used when an operator desires to control peripheral devices by using the voice recognition function for performing a prescribed procedure are set to be valid, and less necessary voice recognition commands are set to be invalid. In the example of FIG. 4, when operator Dr. A performs a laparoscopic cholecystectomy, "release" is set to be valid while "freeze" is set to be invalid among voice recognition commands 55. Thereby, a situation is avoided where the voice recognition command "release" used by the operator Dr. A during laparoscopic cholecystectomy surgery is misrecognized as "freeze" by the system controller 22.

Information set through the window exemplified in FIG. 4 is stored in the storage unit 50. Among pieces of information set through the window exemplified in FIG. 4, the voice recognition command 55 and valid/invalid state 56 corresponding to the voice recognition command 55 are referred to as "voice manipulation setting information" in the explanations below. As explained above, voice manipulation setting information is information that has set whether or not control of peripheral devices is performed (whether it is valid or invalid) by voice recognition in the system controller 22 for each voice recognition command that corresponds to a manipulation command that can be transmitted to peripheral devices in accordance with voice recognition.

FIG. 5 exemplifies voice manipulation setting information set for each piece of operator information 52 and procedure information 53.

Even when "Dr. A", representing the same operator, is set in the operator information 52, for example, if the procedures "laparoscopic cholecystectomy" and "LADG (laparoscopy-assisted distal gastrectomy)", which are different from each other, are set in the operator information 52, the valid/invalid state 56 can be set for each of the procedures for the same voice recognition command 55. When the operators "Dr. A" and "Dr. B", which are different from each other, are set in the operator information 52, the valid/invalid state 56 can be set for each of the operators for the same voice recognition command 55.

It is also possible to employ a configuration in which the validity/invalidity of the voice recognition command 55 is set for each step of surgery in addition to setting it for each piece of operator information 52 and procedure information 53. Steps in surgery will be referred to as "scenes" in the explanations below.

FIG. 6 exemplifies voice manipulation setting information set for each piece of operator information 52, procedure information 53, and scene. FIG. 6 shows an example in which the valid/invalid state 56 of the voice recognition commands 55 has been set for each step, and specifically set for each of "laparotomy" scene and "sutura" scene when the operator "Dr. A" performs laparoscopic cholecystectomy. Scene information 54 in FIG. 6 is information used for identifying scenes.

In, for example, a laparotomy scene, the voice recognition command 55 for controlling the electrocautery scalpel device 13 to be used is set to be valid. In the example shown in FIG. 6, according to the voice manipulation setting information of "laparotomy" of the scene information 54, "DENKI MESU SHUTSURYOKU APPU (increase power for electrocautery scalpel)" and "DENKI MESU SHUTSURYOKU DAUN (decrease power for electrocautery scalpel)", which are used in a laparotomy scene, have been set to be "valid" among the voice recognition commands 55. Meanwhile, control regarding an electrocautery scalpel becomes unnecessary in a subsequent sutura scene. Accordingly, in the example of FIG. 6, the same voice recognition commands 55, i.e., "DENKI MESU SHUTSURYOKU APPU (increase power for electrocautery scalpel)" and "DENKI MESU SHUTSURYOKU DAUN (decrease power for electrocautery scalpel)", have been set to be "invalid" in the voice manipulation setting information of the scene information 54, "sutura" scene.

As described above, for each piece of the scene information 54, the voice recognition commands 55 necessary for a particular scene are set to be valid, whereas the voice recognition commands 55 that are unnecessary are set to be invalid. Thereby, a situation is effectively avoided where input voice commands are misrecognized as unnecessary voice recognition commands 55.

FIG. 7 is a flowchart showing a process in which the control unit 41 of the system controller 22 according to the present embodiment controls peripheral devices on the basis of voice recognition. The control unit 41 starts the process in FIG. 7 in response to the activation of the system controller 22.

Figure 8:
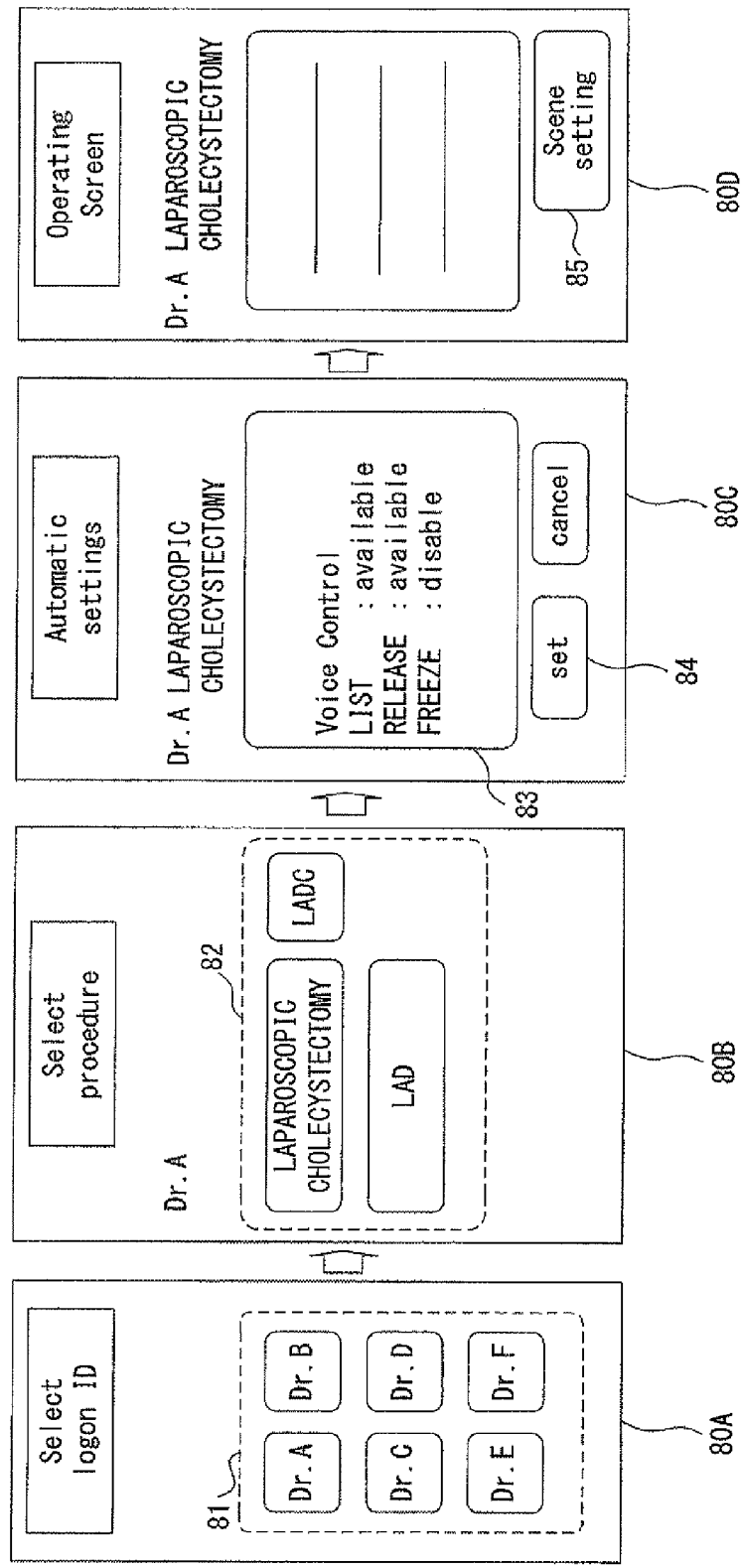
FIG. 8 shows an example of a window displayed on a manipulation panel (first)

First, in step S1, the operator information 52 is identified on the basis of the information input for log-in by an operator. Window 80A in FIG. 8 is a window example displayed on the manipulation panel 21 in step S1. A list 81 including at least one piece of the operator information 52 registered in the system controller 22 is displayed. When the control unit 41 has recognized a log-in of the operator information 52 selected in the list 81, the control unit 41 determines that the operator information 52 whose log-in was recognized has been identified.

In step S2, procedure information is identified. Window 80B in FIG. 8 is a window example displayed on the manipulation panel 21 in step S2. A list 82 including at least one piece of the procedure information 53 registered in the storage unit 50 is displayed for the operator information 52 specified in step S1. When the procedure information 53, representing procedures used in an endoscopic surgery, has been selected from the list 82, it is determined that the selected procedure information 53 has been identified.

In step S3, the valid voice recognition commands 55 that correspond to the operator information 52 and the procedure information 53 specified in step S1 and step S2 are determined. In order to determine valid voice recognition commands 55, voice manipulation setting information corresponding to the operator information 52 and the procedure information 53 is read from the storage unit 50.

Window 80C in FIG. 8 shows a window example displayed on the manipulation panel 21 in step S3. Voice manipulation setting information, read from the storage unit 50 and corresponding to the specified operator information 52 and the procedure information 53, is displayed. A voice recognition command list 83 in the window displays part of the voice recognition commands 55 registered in the storage unit 50 and the corresponding valid/invalid states 56.

When a setting button 84 is pushed by a user such as an operator or the like, the control unit 41 determines the valid voice recognition command 55. Specifically, in the following processes, the control unit 41 determines whether the voice recognition commands 55 are valid or invalid in accordance with the voice manipulation setting information displayed in the window 80C.

In step S4, it is determined whether or not to set a scene. Window 80D in FIG. 8 shows a window example displayed on the manipulation panel 21 in step S4. When a setting button 85 in window 80D has been pushed by a user such as the operator or the like, it is determined that a setting for scene is to be performed. When a setting for scene is not to be performed, a particular process is not performed, and the process proceeds to step S7. When a setting for scene is to be performed, the process proceeds to step S5.

Figure 9:
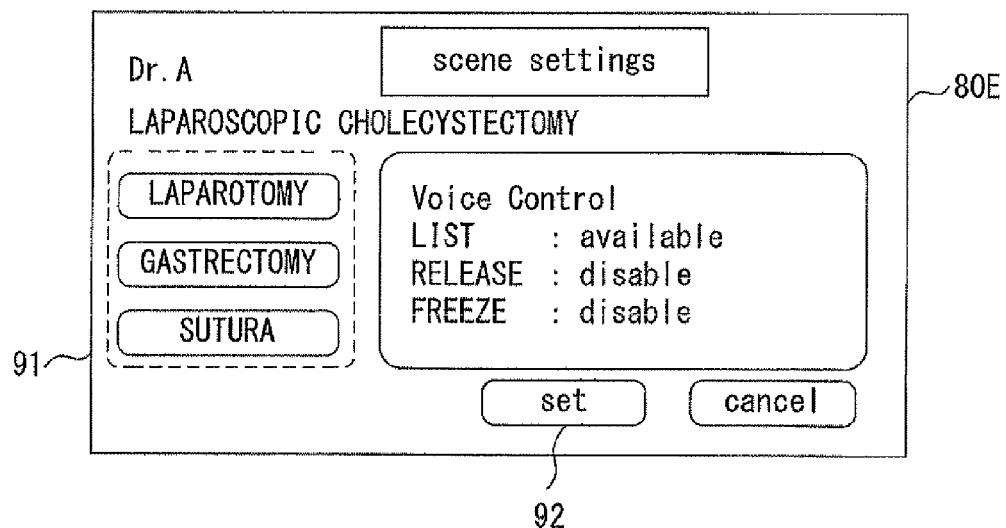
FIG. 9 shows an example of a window displayed on a manipulation panel (second)

In step S5, the process receives the selection of a scene from among scenes set as the voice manipulation setting information. FIG. 9 shows a window example displayed on the manipulation panel 21 in step S5. In window 80e, a list 91 of the voice manipulation setting information for each scene registered in the storage unit 50 for the operator information 52 and the procedure information 53 specified in step S1 and step S2 is displayed. When a scene is selected from the list 91 via the manipulation panel 21 and a setting button 92 has been pushed, the process proceeds to step S6.

In step S6, the valid voice recognition command 55 that corresponds to the scene selected in step S5 is determined. In other words, the control unit 41 determines whether the voice recognition commands 55 are valid or invalid in accordance with the voice manipulation setting information corresponding to the selected scene information 54 in subsequent processes. In step S6, the voice manipulation setting information set before, such as in step S3 and the like, is discarded.

In step S7, it is determined whether or not a voice was input. When there was no input voice, the process returns to step S4. When there was an input voice, the process proceeds to step S8.

In step S8, the signal waveform of an input voice signal is converted into a character string. For converting a digital voice signal waveform into a character string, a known technique is used.

In step S9, a character string obtained in step S8 and the voice recognition command 55 of the voice manipulation setting information set in step S3 or step S6 are compared. It is then determined whether or not the character string is identical to the voice recognition command 55 that is set to be "valid" in the valid/invalid state 56. When the character string is one that does not exist in the valid/invalid state 56, the process proceeds to step S11, and when the character string is identical to the voice recognition command 55 that is set to be "invalid", the process proceeds to step S11 without transmitting command signals to devices. When the character string is identical to the valid voice recognition command 55, the process proceeds to step S10.

In step S10, a manipulation command corresponding to the character string is transmitted to a corresponding peripheral device. In the peripheral device that has received the manipulation command, a control process corresponding to the manipulation command is executed.

In step S11, whether or not the endoscopic surgery has been terminated is determined. When the endoscopic surgery has not been terminated, the process returns to step S4. When the termination of the surgery has been recognized by the manipulation on the manipulation panel 21 by the operator or the like, the process is terminated.

As has been described, according to the system for endoscopic surgery 3 of the present embodiment, information representing whether the voice recognition command 55 for controlling peripheral devices by voice recognition is valid or invalid for each operator, procedure (and scene) is set beforehand. When an input voice signal is converted into a character string for performing voice recognition, if the character string is identical to the voice recognition command 55 that has been set to be valid, the corresponding manipulation command is transmitted to peripheral devices. It is possible to set as valid voice recognition commands that are highly necessary for an operator, a procedure, or a scene, and to set as invalid voice recognition commands that are less necessary. According to this, by setting less necessary commands to be invalid, invalid voice recognition commands 55 are ignored so that the process of transmitting manipulation commands to peripheral devices is stopped even when there is a voice recognition command that sounds similar. Thus, false recognition of the voice recognition command is effectively prevented. And, by preventing false recognition of the voice recognition command, it can prevent the false manipulation command from be transmitted to peripheral devices.

<Second Embodiment>

In the above embodiment, voice recognition determination is performed on the basis of whether or not the character string obtained from an input voice is identical to the voice recognition commands 55 that are set to be valid. By contrast, in the present embodiment, even when a character string obtained from an input voice is not completely identical to the voice recognition commands 55, voice recognition determination is performed with prescribed conditions having been met, which is a different point.

Hereinafter, a method in which the system for endoscopic surgery 3 according to the present embodiment controls peripheral devices on the basis of voice recognition will be explained by focusing on points different from the first embodiment.

In the present embodiment, the configurations of the system for endoscopic surgery 3, the system controller 22, and the control unit 41 are similar to those in the above embodiment, which are shown in FIG. 1 through FIG. 3, and thus explanations thereof will be omitted.

According to the present embodiment, in addition to the voice manipulation setting information, explained in the above embodiment in FIG. 5 and FIG. 6, information representing part of the voice recognition command 55 and the number of characters obtained when the voice recognition command 55 is converted into character strings are stored beforehand for the voice recognition determination process. Voice recognition is performed on the basis of the extent to which characters of a prescribed portion and a number of characters of an entire character string obtained from the waveform of a voice signal input to the system controller 22 are identical to stored information. In the explanations below, information used for comparison with a character string obtained from a waveform, i.e., information that has associated the characters of part of the voice recognition command 55 and the number of the entire command for each of the voice recognition commands 55, is referred to as partial comparison information.

Figure 10:
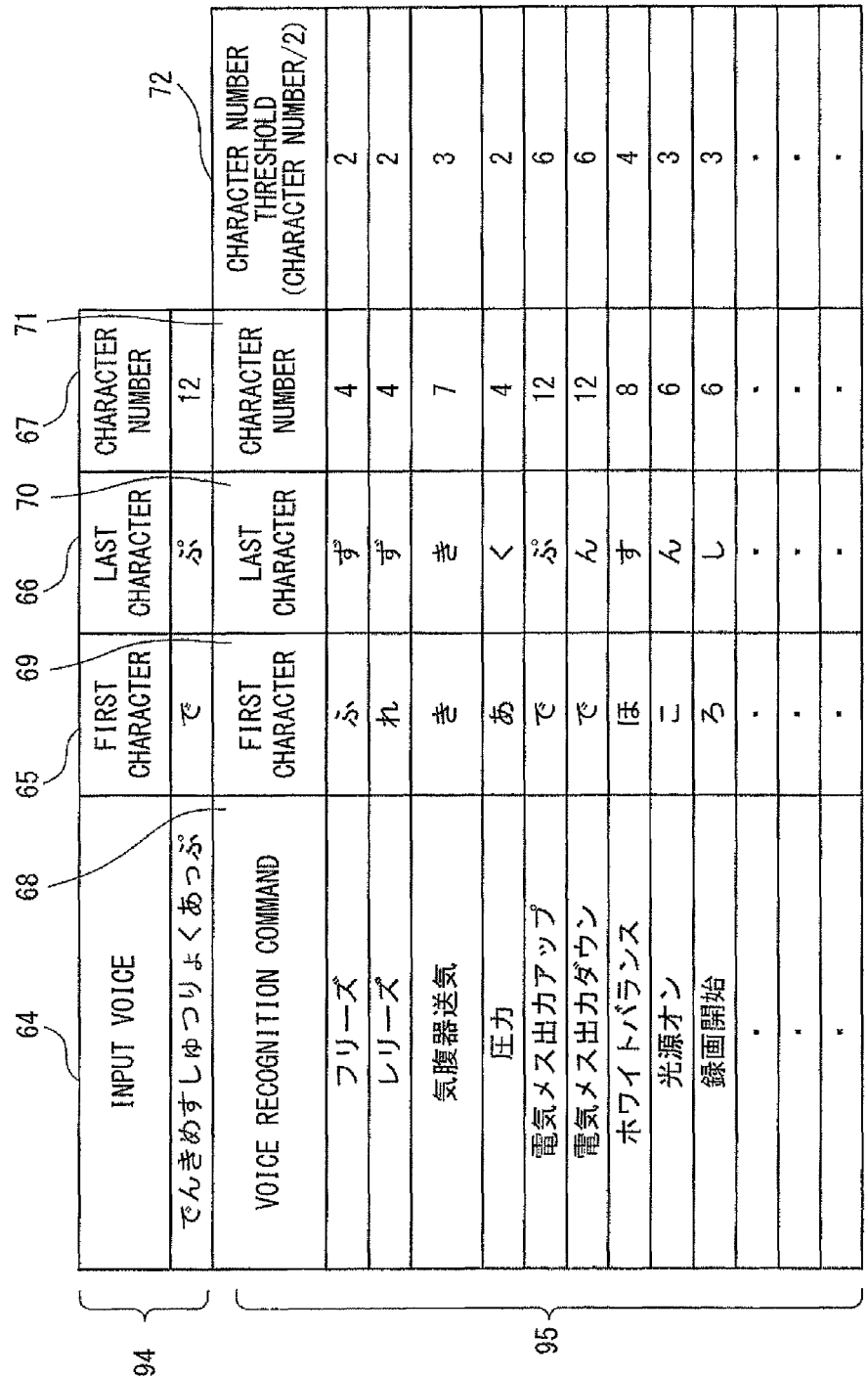
FIG. 10 shows a method of performing voice recognition determination on a character string obtained from a waveform of a voice signal according to a second embodiment.

FIG. 10 shows a method of performing voice recognition determination on a character string obtained from a waveform of a voice signal by referring to partial comparison information of a voice recognition command.

As shown in FIG. 10, in partial comparison information 95, a first character 69, a last character 70, a character number (the number of characters) 71, and a character number threshold 72 are set in association with a voice recognition command 68 for each voice recognition command.

In the partial comparison information 95, for the first character 69 and the last character 70, the first and last characters of a character string obtained when the voice recognition command 68 is expressed as a character string are set. For the character number 71, the number of characters obtained when the voice recognition command 68 is expressed as a character string is set. For the character number threshold 72, the number of characters at a prescribed ratio to the character number 71 is set. In the example shown in FIG. 10, a number of characters that is half the character number 71 is set for the character number threshold 72. The character number threshold 72 is used for comparison with the number of characters of a command obtained by converting voice information into a character string in voice recognition determination.

As an input voice 64 in FIG. 10, character strings obtained from voice signal waveforms are stored. For the input voice 64, the first and last characters, and the number of characters of each character string are obtained to be stored as a first character 65 and a last character 66, and a character number 67, respectively in FIG. 10. In the explanations of the present embodiment below, the input voice 64, the first character 65, the last character 66, and the character number 67 are referred to as input information 94.

Specific explanations will be given for a method of performing voice recognition determination by using information shown in FIG. 10.

FIG. 11 shows a flowchart explaining a process in which the control unit 41 of the system controller 22 according to the present embodiment controls peripheral devices on the basis of voice recognition. By referring to FIG. 11, a method of performing voice recognition on manipulation commands from the input voice 64 to control peripheral devices utilizing the input information 94 and the partial comparison information 95 shown in FIG. 10 will be explained. The process by the control unit 41 shown in FIG. 11 starts in response to the activation of the system controller 22, similarly to the above embodiment. When the system controller 22 has been activated and after the execution of the processes in steps S1 through step S6, the process proceeds to the process in step S21 in FIG. 11, although this is omitted in FIG. 11. Specifically, the process in FIG. 11 is activated after voice manipulation setting information corresponding to the operator information 52, the procedure information 53, and the like, are read and the valid voice recognition commands 55 are determined.

First, in step S21, whether or not there has been voice input is determined. When there was no voice input, the process waits until a voice is input to the control unit 41 of the system controller 22. When there was a voice input, the process proceeds to step S22.

In step S22, the waveform of the input voice signal is converted into a character string.

In step S23, the number of characters is calculated from the character string obtained in step S22. In step S24, the first and last characters are extracted from the character string. The number of characters and the first and last characters obtained in steps S23 and S24 are stored as the character number 67, the first character 65, and the last character 66 of the input information 94 in FIG. 10 in association with the input voice (the character string obtained from the input) 64.

In step S25, whether or not information stored in the partial comparison information 95 includes the first character 69 that is identical to the first character 65 in the input information 94 is determined. When the information does not include the identical first character 69, the process proceeds to step S29. When the information includes the identical first character 69, the process proceeds step S26.

In step S26, whether or not information stored in the partial comparison information 95 includes a last character 70 that is identical to the extracted last character 66 is determined. In this example, the last character 70 of the voice recognition command 68 corresponding to the first character 69 that was determined to be identical to the first character 65 in step S25 is referred to, and whether or not the last character 66 of the input information 94 and the last character 70 are identical to each other is determined. When the last character 66 in the input information 94 and the comparison-target last character 70 are not identical to each other, the process proceeds to step S29. When the last character 66 in the input information 94 and the comparison-target last character 70 are identical to each other, the process proceeds step S27.

In step S27, the character number 67 in the input information 94 is compared with the character number threshold 72 of the voice recognition command 68 having a last character 70 that was determined to be identical to the last character in the input information 94 in step S26. When the character number 67 is smaller than the character number threshold 72, the process proceeds to step S29. When the character number 67 is equal to or greater than the character number threshold 72, the process proceeds to step S28.

Processes in steps S28 and S29 are the same as those in steps S10 and S11 in FIG. 7, respectively.

Note that in step S27 in FIG. 11, it is determined whether or not the character number 67 of the input voice 64 is greater than the character number threshold 72 of the comparison-target voice recognition command 68 in the partial comparison information 95, i.e., whether or not the character number 67 of the input voice 64 is greater than half the character number 71. When the character number 67 of the input voice 64 is equal to or greater than a prescribed ratio of the number of characters of the voice recognition command 68, the validity/invalidity determination of a voice recognition command is performed in the voice recognition determination even when the input voice 64 is not completely identical to the voice recognition command 68. The determination of the validity/invalidity of voice recognition commands is performed by referring to, for example, the voice manipulation setting information shown in FIG. 5 or FIG. 6. A detailed method of determining the validity/invalidity of voice recognition commands is as explained in the above embodiment.

In FIG. 10, (1) shows a case where the input voice 64 and the voice recognition command 68 are identical, while (2) shows a case where input voice 64 and the voice recognition command 68 are not identical. By referring to FIG. 10, effects of the process of determining voice recognition commands corresponding to input voices according to the present embodiment will be explained.

As shown in (1), when the character string of the input voice 64 is identical to the voice recognition command 68, a user such as an operator or the like can control desired peripheral device by voice even when voice recognition determination is performed in the method according to the above described embodiment, shown in FIG. 7. However, when, as in (2), the input voice 64 is not recognized as intended by a user such as an operator or the like, peripheral devices can be controlled by performing voice recognition determination in the method according to the present embodiment.

Specifically, as shown in (2), even when the character string of the input voice 64 has been misrecognized as "でん ぴめすすー りょあぷ (DENPI MESU SU-RYO APU)", the first character 65, i.e., "で (DE)", and the last character 66, i.e., "ぷ (PU)", are identical to the first character 69 and the last character 70 of the voice recognition command 68 "電気メス出力アップ (DENKI MESU SHUT-SURYOKU APPU)", respectively. Meanwhile, the character number 67 of the input voice 64 has been recognized as 10, which is different from the character number of "電気メス出力アップ 電気メス出力アップ (DENKI MESU SHUTSURYOKU APPU)", i.e., 12. Even in this case, the number is greater than 6, the character number threshold 72 of DENKI MESU SHUTSURYOKU APPU". Thereby, even when the character string of the input voice 64 is not identical to a voice recognition command completely, it is possible to determine that the voice recognition command "電気メス出力アップ 電気メス出力アップ (DENKI MESU SHUTSURYOKU APPU)" has been input by the input voice 64.

There are some cases where sound included in the middle of the voice recognition command 68 or the like made of a large number of characters is not able to be picked up correctly due to noise, etc., leading to recognition as wrong characters or character omissions. Even in such a case, when part, e.g., the first and last, of the characters is identical and the number of characters are close to a voice recognition command at least at a prescribed ratio, it is determined that the voice recognition command has been input by voice so as to perform voice recognition determination. Thereby, the frequency at which voice recognition commands are determined to be non-recognizable is reduced.

As described above, according to the system for endoscopic surgery 3 of the present embodiment, all portions of the input voice 64 do not have to be identical to the voice recognition command 68 when voice recognition is performed and a manipulation command is transmitted to peripheral devices. It is determined whether or not there exists a voice recognition command 68 that has a portion identical to a corresponding portion (the first character and the last character in the above example) of the input voice 64 and that has at least a prescribed ratio of the number of characters corresponding to the input voice 64. When partial comparison information includes the voice recognition command 68 that meets these conditions, voice recognition determination is performed for the voice recognition command 68 that meets these conditions. It is possible to perform voice recognition determination so as to transmit a corresponding manipulation command to peripheral devices even when not all characters of the input voice 64 are identical to those of the voice recognition command 68. This leads to an increase in the recognition rate of voice recognition commands in addition to the effects by the voice recognition determination process according to the above embodiment.

Note that while the above example compares the first and last characters of a character string with those of voice recognition commands, the scope of the present invention is not limited to this example. Also, comparison is not limited to comparison between a single character and a single character. Further, while the above example employs, as the character number threshold 72, a value equal to half the number of characters of the voice recognition command 68, thresholds are not limited to half the number of characters of the voice recognition command 68. Also, while the above example compares the number of characters of the input voice 64 with a threshold, the number of syllables of the input voice 64 may be compared with a threshold set in accordance with the number of syllables of the voice recognition commands 68.

<Third Embodiment>

The above embodiments process a voice, as it is, that was input through the microphone 33 shown in FIG. 1, and uses the result for the voice recognition determination process. In contrast, in the present embodiment, the system controller 22 adjusts a voice input from the microphone 33 into a volume level appropriate for performing the voice recognition determination process, which is a different point.

Hereinafter, a method in which the system for endoscopic surgery 3 according to the present embodiment controls peripheral devices on the basis of voice recognition will be explained by focusing on points different from the first embodiment.

In the present embodiment, the configurations of the system for endoscopic surgery 3 and the system controller 22 are similar to those of the above embodiment, which are shown in FIG. 1 and FIG. 2, and thus explanations thereof will be omitted.

Figure 12:
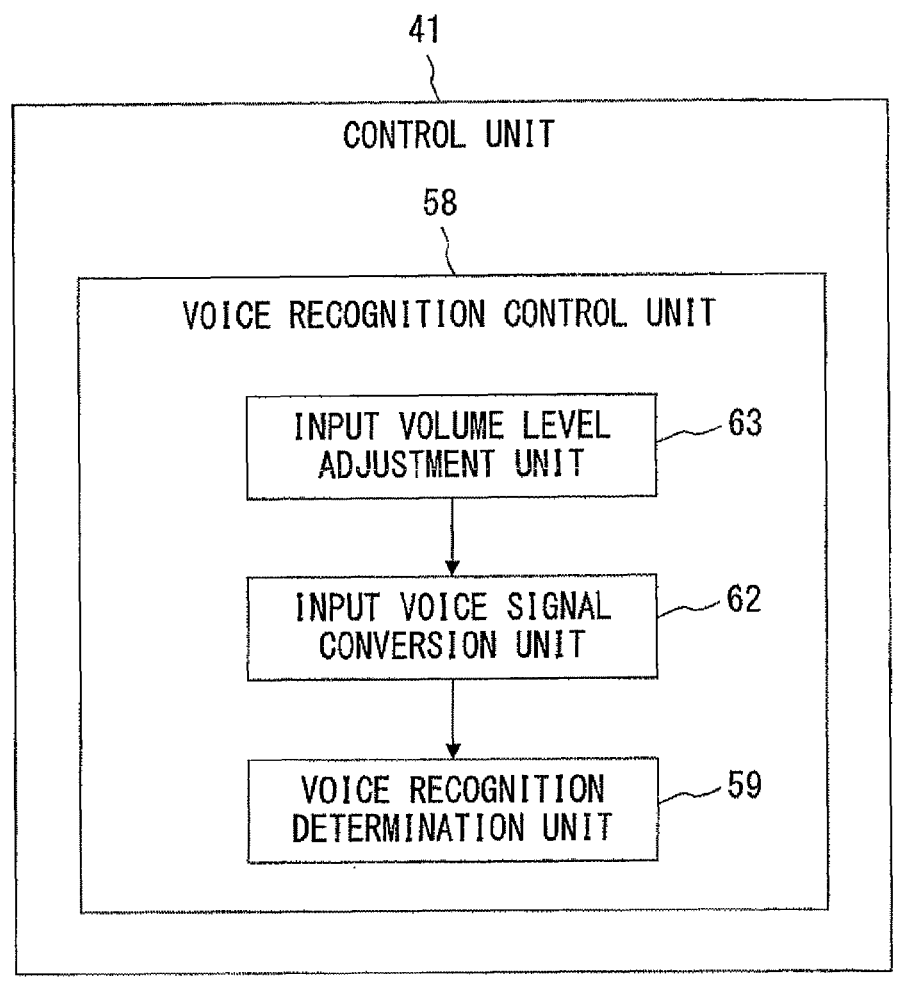
FIG. 12 is a function block diagram of a control unit according to a third embodiment.

FIG. 12 is a function block diagram of the control unit 41. The control unit 41 shown in FIG. 12 includes an input volume level adjustment unit 63 in the voice recognition control unit 58 in addition to the input voice signal conversion unit 62 and the voice recognition determination unit 59, which is a different point from the above embodiment.

The input volume level adjustment unit 63 measures the volume level from the waveform of a digital voice signal input through the A/D conversion unit 45 in FIG. 2, and performs adjustment so that the measured volume level is included in a prescribed range. A voice signal that has received volume level adjustment is input to the input voice signal conversion unit 62. Operations of the input voice signal conversion unit 62 and the voice recognition determination unit 59 are similar to those in the above embodiment.

Detailed explanations will be given further for the voice recognition determination method according to the present embodiment by referring to flowcharts.

Figure 13:
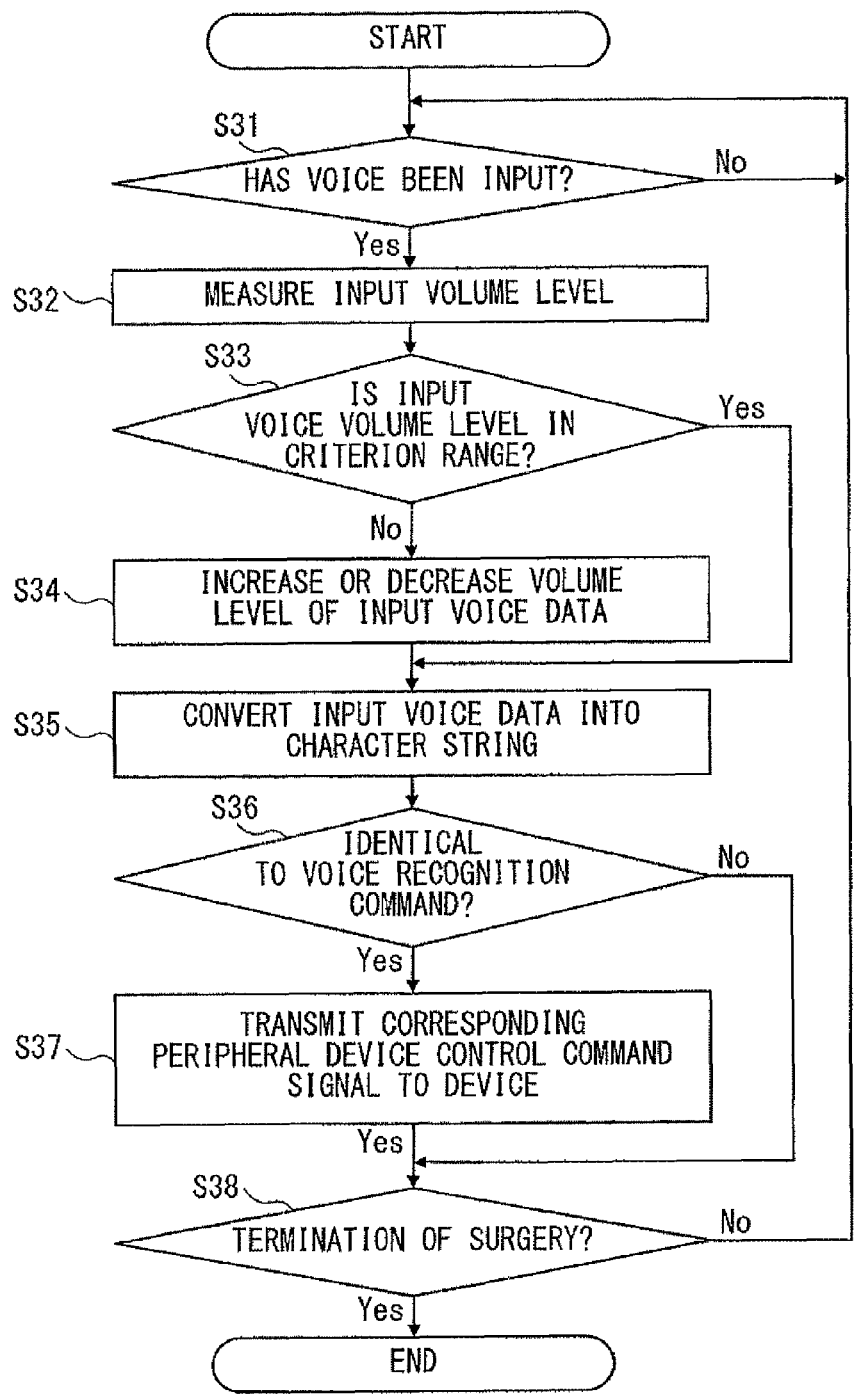
FIG. 13 shows a flowchart explaining a process in which the control unit of a system controller according to the third embodiment performs control of peripheral devices on the basis of voice recognition.

FIG. 13 shows a flowchart explaining a process in which the control unit 41 of the system controller 22 according to the present embodiment performs control of peripheral devices on the basis of voice recognition. Specific explanations will be given for a method of performing voice recognition determination after adjusting the volume level of a voice signal. Similarly to the above embodiments, the process by the control unit 41 shown in FIG. 13 starts in response to the activation of the system controller 22. Also, when the system controller 22 has been activated, the process proceeds to the process in step S31 in FIG. 13 after the execution of the processes in step S1 through step S6 in FIG. 7, although this is omitted in FIG. 13. Specifically, the process in FIG. 13 is activated after voice manipulation setting information corresponding to the operator information 52, the procedure information 53, and the like are read and the valid voice recognition commands 55 are determined.

First, in step S31, whether or not there has been voice input is determined. When there was no voice input, the process waits until a voice is input to the control unit 41 of the system controller 22, similarly to step S21 in FIG. 11. When there was a voice input, the process proceeds to the next step.

In step S32, the input volume level is measured from the waveform of a digital voice signal input to the control unit 41 from the A/D conversion unit 45. A known technique is used for measuring an input volume level.

In step S33, it is determined whether or not the measured volume level meets a volume level value criterion stored beforehand in the storage unit 50. A volume level value criterion includes, for example, the maximum and minimum values of a volume level that is appropriate for voice recognition. When a volume level meets the value criterion, the process proceeds to step S35 without performing any particular processes. When the volume level does not meet the value criterion, the process proceeds to step S34.

In step S34, the volume level of an input voice signal is increased or decreased so that the volume level of the input voice data meets the volume level value criterion.

The processes in and after step S35 are similar to those in and after step S8 in FIG. 7.

As described above, according to the system for endoscopic surgery 3 of the present embodiment, the volume level of an input voice is adjusted so that it meets the volume level value criterion if necessary, and thereafter the voice recognition determination is executed so as to control peripheral devices on the basis of voice recognition. When, for example, an input volume level is low, the input voice may be not able to be converted into a character string if it is not adjusted and the voice may be determined to be non-recognizable. The present embodiment can prevent this situation effectively. Also, even when an input value level is high, the input volume level is adjusted to be within a range appropriate to voice recognition software. This leads to effective avoidance of an increase in the possibility that input information will not be recognized, in addition to the effect achieved by the voice recognition determination process according to the above embodiments.

Also, in the above example, a process of adjusting a volume level is applied to the voice recognition determination process according to the first embodiment. However, the scope of the present invention is not limited to this. For example, the volume level adjustment process may be applied to the voice determination process according to the second embodiment.

<Fourth Embodiment>

The first embodiment can set the validity or invalidity of voice recognition commands for each operator, each procedure, and each scene. The present embodiment can set the validity or invalidity of voice recognition commands for each surgery room, which is a different point.

Hereinafter, a method in which the system for endoscopic surgery 3 according to the present embodiment controls peripheral devices on the basis of voice recognition will be explained by focusing on points different from the first embodiment.

In the present embodiment, the configurations of the system for endoscopic surgery 3 and the system controller 22 are similar to those of the above embodiment, which are shown in FIG. 1 through FIG. 3, and thus explanations thereof will be omitted.

However, in the present embodiment, the valid/invalid state 56 for each voice recognition command 55 can be set for each piece of surgery room information used for identifying surgery rooms in the voice manipulation setting information registered beforehand in the storage unit 50. For example, different peripheral devices and such are necessary for each type of endoscopic surgery, and a surgery room is sometimes provided with equipment appropriate to each particular surgery. In such a case, voice recognition commands 55 that are highly necessary are set to be valid in accordance with types of endoscopic surgeries for each surgery room while setting unnecessary voice recognition commands 55 to be invalid so as to avoid misrecognition more effectively.

In an example, the valid/invalid state 56 of the voice recognition commands 55 can be set for each scene. Hereinafter, specific explanations will be given for a method of determining the voice recognition commands 55 that are valid for each scene, and performing voice recognition determination so as to control peripheral devices, by referring to a flowchart.

Figure 14:
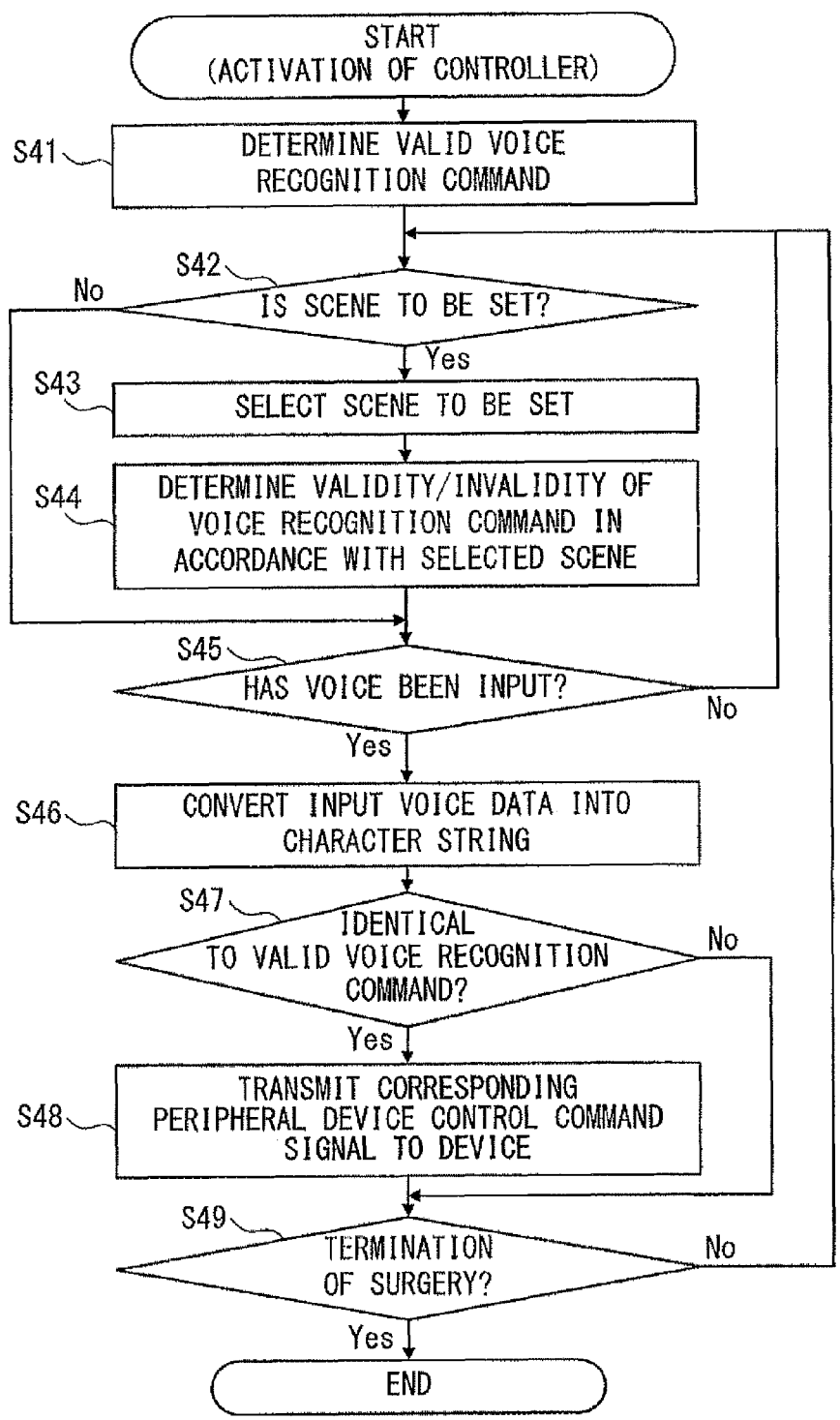
FIG. 14 is a flowchart showing a process in which a control unit of a system controller according to a fourth embodiment controls peripheral devices on the basis of voice recognition.

FIG. 14 is a flowchart showing a process in which the control unit 41 of the system controller 22 according to the present embodiment controls peripheral devices on the basis of voice recognition. The control unit 41 starts the process in FIG. 14 in response to detecting, through the display I/F 51 or the like, that an operator has entered a prescribed surgery room or that the system controller 22 installed in a prescribed surgery room has been activated. When the control unit 41 has read the voice manipulation information corresponding to the surgery room, the control unit 41 of the system controller 22 executes the process in step S41.

In step S41, the valid voice recognition commands 55 are determined. A method of determining the valid voice recognition commands 55 is as explained in step S3 in FIG. 7.

In step S42, it is determined whether or not to set scenes. As described above, voice manipulation setting information is set for each surgery room and each scene. When scene setting is not performed, no processes are performed particularly, and the process proceeds to step S45. When scene setting is performed, the process proceeds to step S43.

The processes in and after step S43 are similar to those in and after step S5 in FIG. 7.

As described above, according to the system for endoscopic surgery 3 of the present embodiment, the validity and invalidity of the voice recognition command 55 can be set by using voice manipulation information for each surgery room. By setting voice recognition commands used often in a particular surgery to be valid and setting those not used so often to be invalid, the same effects are achieved as those achieved by the system for endoscopic surgery 3 of the first embodiment.

In addition to the above, various modifications and alterations are possible without departing from the spirit of the present invention. For example, some constituent elements may be omitted from the configurations shown in the above respective embodiments, and also different constituent elements may be combined appropriately across respective embodiments.

Further, in the system for endoscopic surgery 3 according to the above first through fourth embodiments, a configuration may be employed in which units that respectively measure and detect the direction of an operator's eyes and a monitor for voice manipulation are included so that when the operator looks at the voice manipulation monitor for performing voice manipulation, voice manipulations are made valid. This effectively avoids a situation where the microphone 33 in FIG. 1 performs voice recognition determination by mistake from conversations and such that are not intended to be used for voice manipulation of peripheral devices and wrong manipulation commands are transmitted to peripheral devices, causing malfunctions.

What is claimed is:

1. A system for endoscopic surgery having a function of controlling, through voice recognition, a connected peripheral device, comprising:

storage unit that stores a command for controlling the peripheral device and whether or not the command is valid or invalid in an associated manner for each combination of an operator and a procedure of an endoscopic surgery;

a specification unit that receives specification of the operator and the procedure;

a conversion unit that recognizes an input voice, and converts the voice into a voice command;

a determination unit that refers to the storage unit, and determines whether or not the voice command obtained by the conversion unit is identical to a command that has been set to be valid for the combination of the operator and the procedure specified by the specification unit;

a transmission unit that halts a transmission process to a peripheral device that corresponds to a command that has been determined to be invalid by the determination unit; and a scene specification unit that receives specification of a scene of the endoscopic surgery, wherein:

in the conversion unit, a voice command is information obtained by conversion into a character string;

the storage unit stores, for each of the operators and the procedures, whether each of the commands is valid or invalid for each of the scenes; and when a scene has been received in the scene specification unit, the determination unit determines whether or not the character string is identical to a command that has been set to be valid in the storage unit for the received scene for the operator and the procedure received in the specification unit.

2. The system for endoscopic surgery according to claim 1, wherein:

the determination unit determines whether or not a character string obtained in the conversion unit is identical to a command that has been set to be valid in the storage unit on the basis of whether or not the character string is partially identical to the command stored in the storage unit and whether or not a number of characters or a number of syllables of the character string is equal to or greater than a prescribed ratio of a number of characters or a number of syllables of the command stored in the storage unit.

3. The system for endoscopic surgery according to claim 1, further comprising:

an adjustment unit that measures a volume level of an input voice, and adjusts the volume level so that the measured volume level is within a prescribed range, wherein:

the conversion unit performs a process of converting the voice of which volume level has adjusted by the adjustment unit into a character string.

4. A system for endoscopic surgery having a function of controlling, through voice recognition, a connected peripheral device, comprising:

a storage unit that stores a command for controlling the peripheral device and whether or not the command is valid or invalid in an associated manner for each combination of an operator and a procedure of an endoscopic surgery;

a specification unit that receives specification of the operator and the ; procedure a conversion unit that recognizes an input voice, and converts the voice into a voice command;

a determination unit that refers to the storage unit, and determines whether or not the voice command obtained by the conversion unit is identical to a command that has been set to be valid for the combination of the operator and the procedure specified by the specification unit;

a transmission unit that transmits a command that has been determined to be identical by the determination unit, to a corresponding peripheral device; and a scene specification unit that receives specification of a scene of the endoscopic surgery, wherein:

in the conversion unit, a voice command is information obtained by conversion into a character string;

the storage unit stores, for each of the operators and the procedures, whether each of the commands is valid or invalid for each of the scenes; and when a scene has been received in the scene specification unit, the determination unit determines whether or not the character string is identical to a command that has been set to be valid in the storage unit for the received scene for the operator and the procedure received in the specification unit.

\* \* \* \* \*